United States Patent [19]

Cox et al.

[11] Patent Number: 4,824,644

[45] Date of Patent: Apr. 25, 1989

[54] RECIRCULATING HIGH VELOCITY HOT AIR STERILIZING DEVICE HAVING IMPROVED INTERNAL INSULATION STRUCTURE

[75] Inventors: M. Keith Cox, Dallas, Tex.; Virgil L. Archer, Boyce City, Okla.

[73] Assignee: Archeraire Industries, Inc., Dallas, Tex.

[21] Appl. No.: 106,182

[22] Filed: Oct. 8, 1987

Related U.S. Application Data

[63] Continuation-in-part of Ser. No. 44,909, Apr. 30, 1987.

[51] Int. Cl.$^4$ ............................................... A61L 2/00
[52] U.S. Cl. ..................................... 422/300; 422/292; 126/21 A; 126/21 R; 219/400
[58] Field of Search ................. 422/1, 7, 28, 292, 295, 422/297, 300; 219/400; 126/21 R, 21 A; 426/521, 523, 407

[56] References Cited

U.S. PATENT DOCUMENTS

| | | | |
|---|---|---|---|
| 2,480,227 | 8/1949 | Derr | 34/45 |
| 3,478,758 | 11/1969 | Davies | 422/300 |
| 3,489,505 | 1/1970 | Shumann et al. | 422/292 |
| 3,839,622 | 10/1974 | Mastin | 219/400 |
| 4,039,776 | 8/1977 | Roderick | 219/401 |
| 4,377,109 | 3/1983 | Brown et al. | 99/401 |
| 4,395,233 | 7/1983 | Smith et al. | 432/176 |
| 4,430,989 | 2/1984 | Narang et al. | 126/273 |
| 4,435,194 | 3/1984 | Picard | 422/295 |
| 4,455,478 | 6/1984 | Guibert | 219/400 |
| 4,581,989 | 4/1986 | Swartley | 99/346 |

FOREIGN PATENT DOCUMENTS

| | | |
|---|---|---|
| 865937 | 9/1953 | Fed. Rep. of Germany . |
| 1128601 | 9/1956 | Fed. Rep. of Germany . |
| 969018 | 7/1958 | Fed. Rep. of Germany . |
| 1121675 | 8/1956 | France . |

*Primary Examiner*—David L. Lacey
*Assistant Examiner*—Lori-Ann Johnson
*Attorney, Agent, or Firm*—Hubbard, Thurman, Turner & Tucker

[57] ABSTRACT

A recirculating, high velocity hot impingement air sterilizer has an inner housing that defines a chamber adapted to receive dental instruments or the like to be sterilized by hot impingement air jets flowed through the chamber by a compact fan, duct and heating coil assembly exteriorly secured to the inner housing. A specially designed insulating jacket structure envelopes and removably receives the inner housing, the jacket structure having a flexible, hollow outer skin portion filled with and captively retaining a suitable insulating material. The jacketed inner housing is received within an outer housing and defines therein a cooling space which extends around a major portion of the insulating jacket structure. Cooling air is flowed through such cooling space by a small fan secured to the inner surface of a removable back panel portion of the outer housing. By simply removing the back panel portion, and then removing a back portion of the insulating jacket, access to the main fan and heating coil structure is quickly and easily provided to repair or replace the same without removing the inner housing. The flexible outer skin portion of the insulating jacket prevents the insulating material from damage or dislodgement into either housing during the repair or replacement of the main fan and heating coil structure.

12 Claims, 3 Drawing Sheets

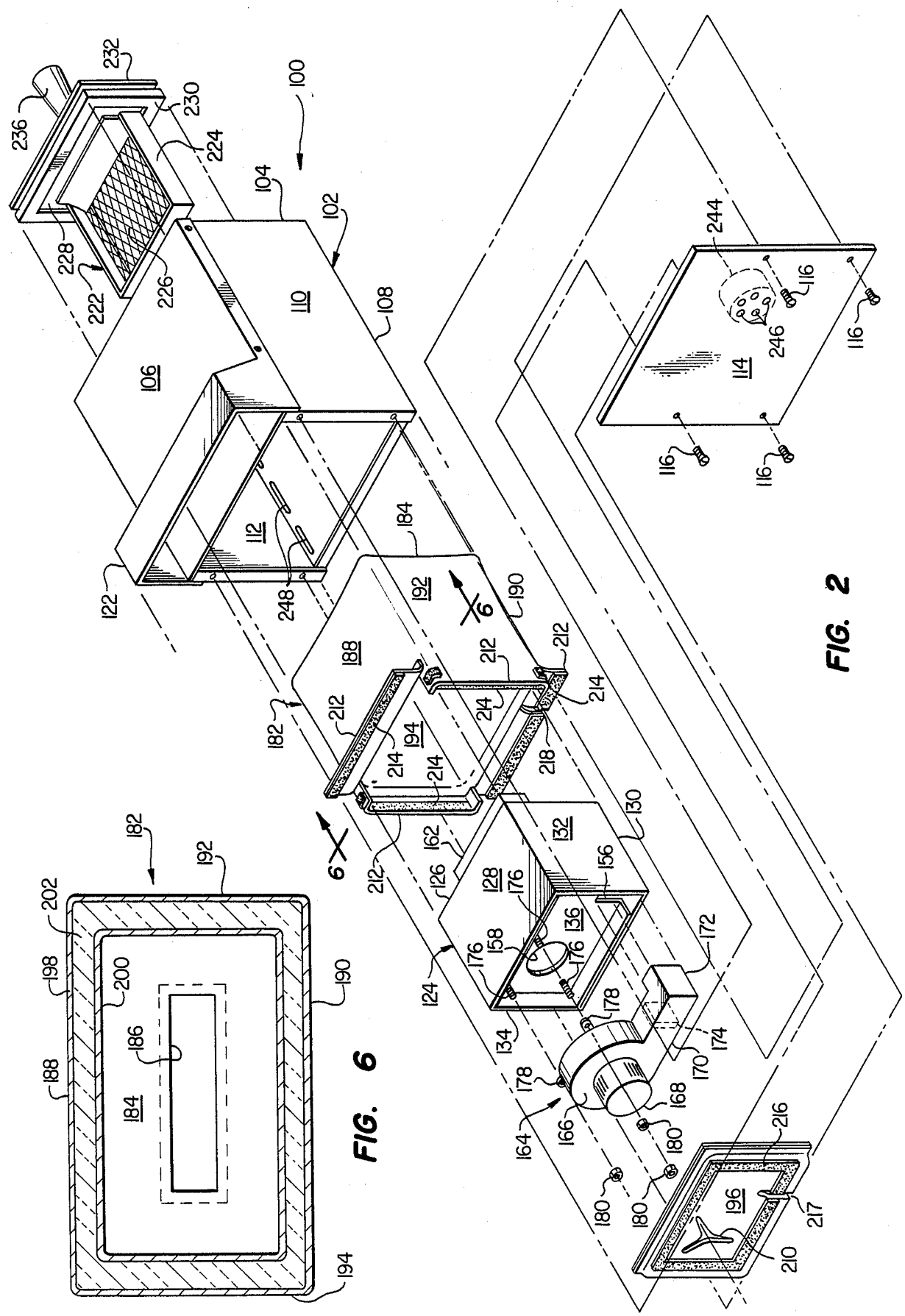

RECIRCULATING HIGH VELOCITY HOT AIR STERILIZING DEVICE HAVING IMPROVED INTERNAL INSULATION STRUCTURE

CROSS-REFERENCE TO RELATED APPLICATION

This application is a continuation-in-part of my co-pending U.S. application Ser. No. 044,909 filed on Apr. 30, 1987 and entitled: "Recirculating High Velocity Hot Air Sterilization Device", such pending application being incorporated herein by reference.

BACKGROUND OF THE INVENTION

The present invention relates generally to hot air sterilization devices, and more particularly provides a device which utilizes recirculating, high velocity hot impingement air to sterilize medical and dental instruments or the like, and is provided with an improved internal insulation structure together with a variety of other structural improvements.

The sterilizer disclosed and described in my commonly assigned copending U.S. application Ser. No. 044,909, which is incorporated herein by reference, has proven to be quite effective in rapidly, inexpensively and non-corrosively sterilizing and depyrogenating metal dental and surgical instruments. As described in such copending application, the sterilization of the instruments is achieved utilizing a recirculating flow of high velocity, hot air impingement jets within a sterilization chamber formed in an inner housing portion of the sterilizer. This inner housing is disposed within an outer housing which forms with the inner housing an insulation space in which sheets of suitable fibrous insulating material are disposed. Suitable cooling fan means (not shown) were used to circulate cooling air around this insulation space within the outer housing.

The hot sterilizing air is recirculated within the sterilization chamber by means of an air circulating fan disposed within the outer housing and having an inlet communicating with the sterilization chamber. Air discharged from the fan is forced into a supply plenum formed in the inner housing beneath the sterilization chamber. The recirculating air is heated by means of an electric heating element disposed in the supply plenum.

In the course of developing this particular sterilizer, it has been found that this insulation, air delivery and heating structure creates certain maintenance disadvantages. For example, when it becomes necessary to remove or repair the recirculating air fan disposed within the outer housing, exposed portions of the fibrous insulation sheets are often damaged, causing small pieces thereof to be dislodged and fall into the interior of the outer housing. Additionally, to repair or replace the electric air heating element, it was necessary to provide access to the interior of the supply plenum disposed within the inner housing. Further, cooling air flow within the outer housing often entrained dislodged bits of fibrous insulation causing them, in some instances, to find their way into the inner housing sterilization chamber and interfere with the sterilization process therein.

It is accordingly an object of the present invention to provide an improved hot air impingement sterilizer of the type described in my co-pending U.S. application Ser. No. 044,909 in which the above-mentioned and other maintenance and access limitations and disadvantages are eliminated or minimized.

SUMMARY OF THE INVENTION

In carrying out principles of the present invention, in accordance with a preferred embodiment thereof, a recirculating, high velocity heated impingement air sterilizer is provided for sterilizing metal dental and surgical instruments or the like. The sterilizer includes a metal inner housing having a sterilization chamber separated from a supply air plenum by a corrugated jet plate member having a series of jet-forming openings formed therethrough, the sterilization chamber being partially bounded by a corrugated deflection wall spaced apart from and extending generally parallel to the jet plate member. The inner housing has a back wall with a circular return air opening formed therethrough and communicating with the sterilization chamber, and a rectangular supply opening which communicates with the supply air plenum. Removably secured to the back wall of the inner housing is a fan, duct and heating element assembly which includes a recirculating fan having a motor, an outlet, and an inlet which communicates with the sterilization chamber through the return air opening. Connected to the outlet of the recirculating fan is a supply duct which has an open discharge end that communicates with the supply air plenum through the supply air opening. Operatively disposed within the supply duct is an electric heating coil.

The sterilizer also includes an outer housing which envelopes the inner housing and has a front wall opening that communicates with the sterilization chamber through an inlet passage formed on the front wall of the inner housing. The back wall of the outer housing is removable to provide access to the inner housing and the fan, duct and heating element assembly removably secured to its rear wall.

The inner housing, and the fan, duct and heating element assembly, are removably received within a unique insulating jacket structure disposed within the outer housing. The jacket structure includes a flexible, hollow outer shell in which is captively retained a quantity of flexible insulation material. The jacket structure has a rear access wall which is removable from the balance of the jacket structure and extends across the fan, duct and coil assembly, with the fan motor projecting outwardly through a slit formed in the access wall section. In assembling the sterilizer, the inner housing and the circulating assembly are inserted into the jacket structure, and the access wall portion of the structure is moved into place. The jacketed inner housing and assembly are then inserted into the outer housing and secured therein. The back wall of the outer housing is then secured to the balance of the outer housing.

The insulating jacket structure, and the configuration and positioning of the fan, duct and coil assembly, permits rapid and simple access to the fan, motor and heating coil for replacement and maintenance purposes. All that is necessary is to remove the back wall of the outer housing and the back wall of the insulating jacket structure so that the entire fan, duct and coil assembly can be quickly removed. Removal or repair of the assembly does not damage the insulation which is captively retained within the flexible outer shell portion of the insulation jacket structure, or cause bits of insulation to be shredded away and dislodged into the interior of the sterilizer.

During operation of the sterilizer, instruments or the like to be sterilized are placed in a mutually spaced relationship on a wire mesh tray which is inserted through the aligned inner and outer housing openings into the sterilization chamber. The recirculating fan forces heated air into the air supply plenum and then upwardly through the openings in the jet plate to form a series of relatively high velocity heated air jets which are directed toward the deflection wall. Some of these jets immediately impinge upon first surface portions of the supported instruments within the sterilization chamber, while others of the jets bypass the instruments and strike the deflection wall. The jets striking the deflection wall are rearwardly deflected therefrom, in the form of relatively high velocity redirected jets, onto opposite surface portions of the instruments. This combination of jet impingement upon opposite side surfaces of the supported instruments creates a turbulent air layer around the instruments to rapidly sterilize and depyrogenate them. The turbulent air layer surrounding the instruments is continuously drawn across the instruments in a direction generally transverse to the jet flow direction to create a "scrubbing" action on the instruments to further enhance the sterilization and depyrogenation thereof.

The insulation jacket structure defines within the outer housing a cooling cavity which extends around the front, back, top and sides of the jacket structure. A flow of ambient cooling air is forced through the cooling cavity by a small cooling fan supported on the interior surface of the rear outer housing wall. Ambient air is drawn into the cooling fan through small openings formed in the back outer housing wall, and is then forced through the cooling cavity and discharged outwardly through a series of small cooling air discharge openings formed through the bottom wall of the outer housing. The outer shell portion of the insulating jacket structure prevents bits of the fibrous insulation captively retained therein from being dislodged by and entrained in the cooling air flow and thereby finding their way into the inner housing sterilization chamber and interfering with the sterilization process therein.

BRIEF DESCRIPTION OF THE DRAWINGS

FIG. 2 is an exploded perspective view of the sterilizer and illustrates a unique internal insulating jacket structure incorporated therein;

FIG. 6 is an enlarged scale cross-sectional view taken through the insulating jacket structure along line 6—6 of FIG. 2.

DETAILED DESCRIPTION

Figure 1:
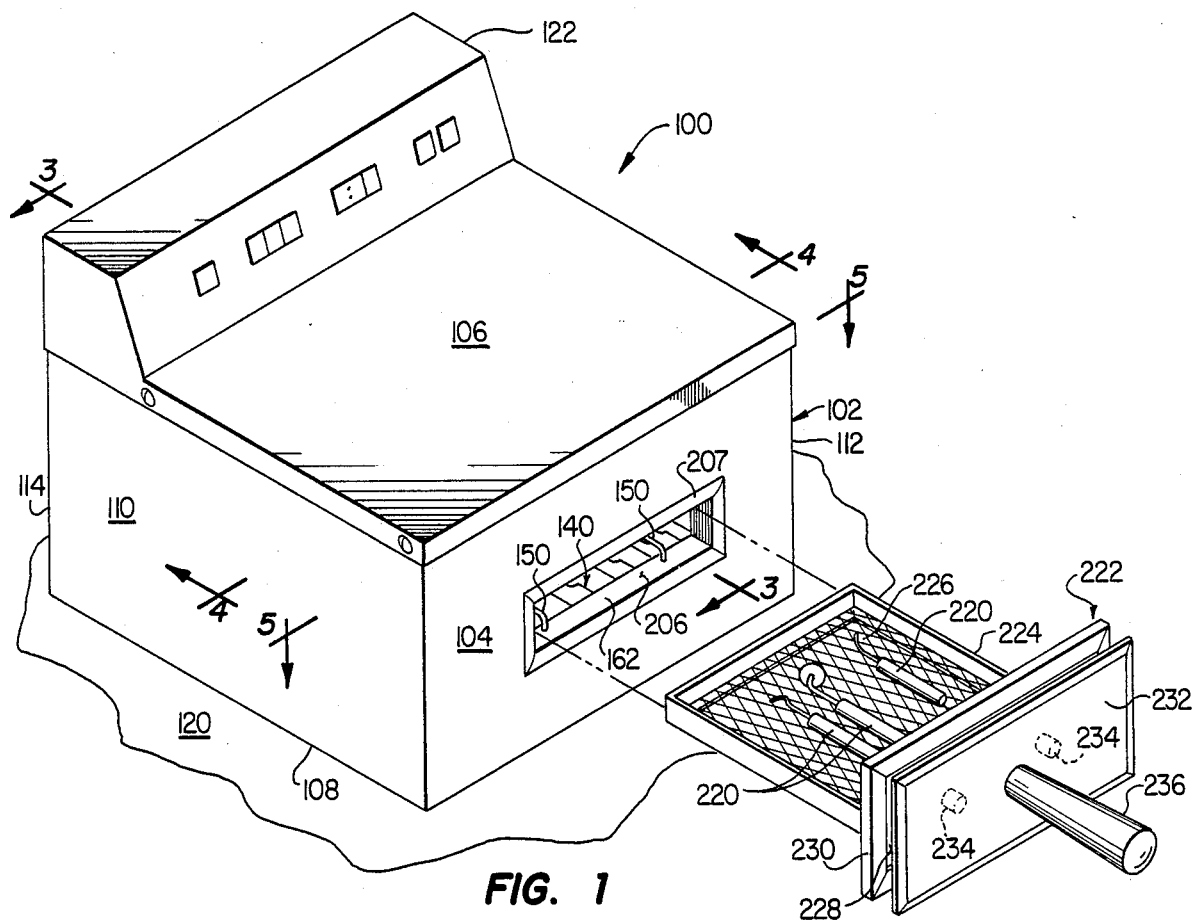
FIG. 1 is a perspective view of a recirculating, high velocity hot impingement air instrument sterilizer which embodies principles of the present invention, an instrument-holding tray portion of the sterilizer being removed for illustrative purposes.

Perspectively illustrated in partially exploded fashion in FIG. 1 is an improved sterilizer 100 which embodies principles of the present invention and is utilized to sterilize and depyrogenate medical and dental instruments or the like using a recirculating flow of high velocity hot air impingement jets. In operation, the sterilizer 100 is similar to that of the sterilizers disclosed and described in my copending U.S. application Ser. No. 044,909 which is incorporated herein by reference. However, as will now be described, the sterilizer 100 has incorporated therein various unique structural features which provide for significantly easier maintenance and repair of certain internal components of the sterilizer.

Referring now to FIGS. 1 and 2, the sterilizer 100 includes a metal outer housing 102 (preferably of a magnetic stainless steel material) having a generally rectangular cross-section, a front wall 104, top and bottom walls 106 and 108, left and right side walls 110 and 112, and a back access wall 114 which is removably securable to the balance of the outer housing by means of suitable fastening members such as screws 116. Adjacent the corners of the lower wall 108 are four small, depending support legs 118 (FIGS. 3 and 4) adapted to rest upon a supporting surface such as a table 120 and elevate the lower wall 108 relative to such support surface. Extending upwardly from a rear portion of the upper housing wall 106 is a control panel portion 122 of the sterilizer which is utilized, in a manner not pertinent to the present invention, to control the operation of a subsequently described heating coil element disposed within the outer housing.

Figure 3:
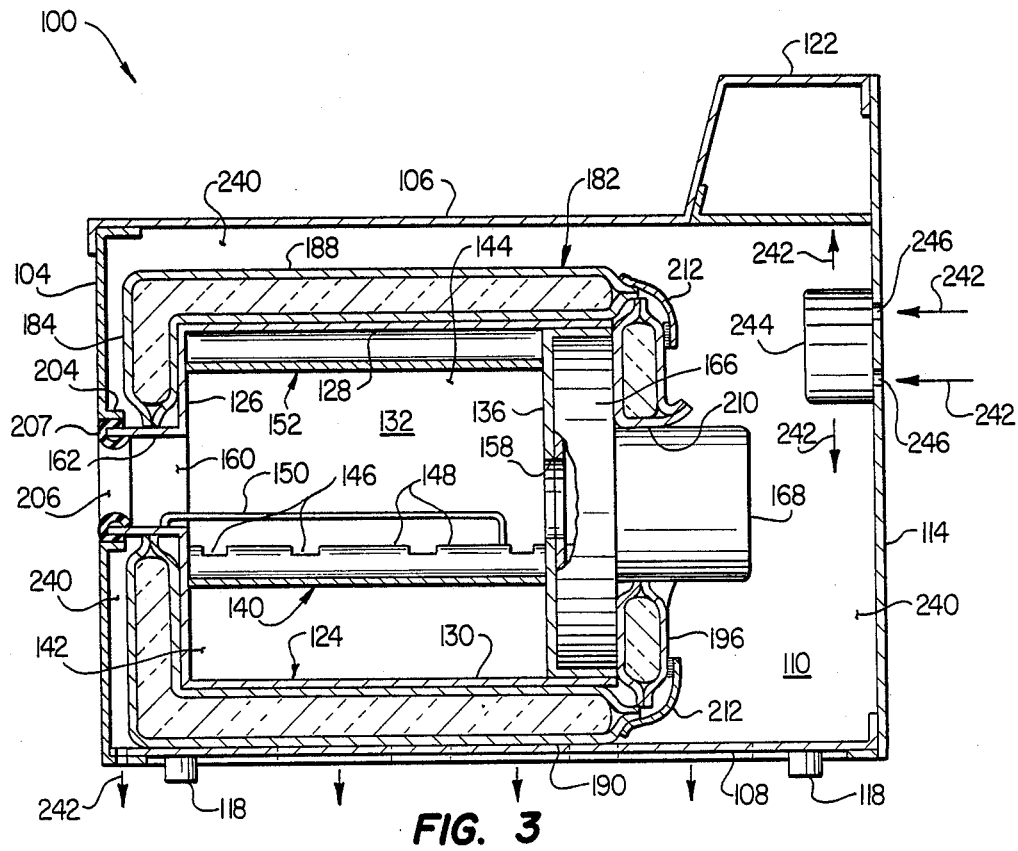
FIG. 3 is an enlarged scale cross-sectional view, partially in elevation, through the sterilizer, with the tray portion removed therefrom, taken along line 3—3 of FIG. 1.
Figures 4, 5:
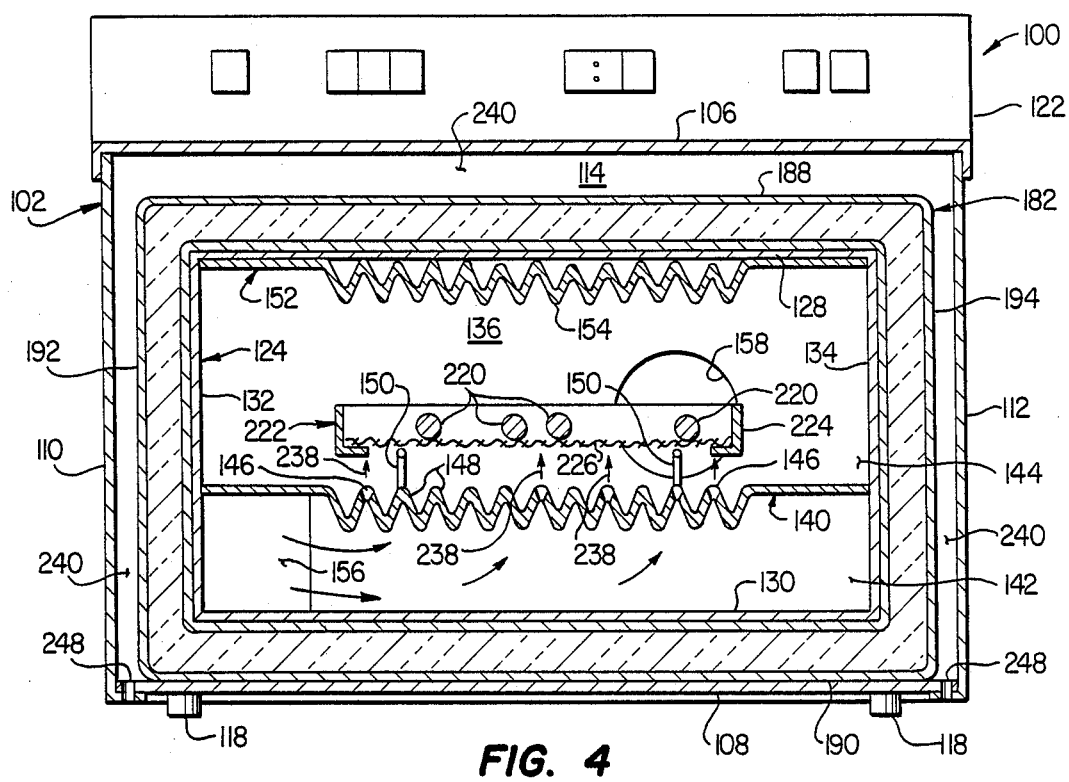
FIG. 4 is an enlarged scale cross-sectional view through the sterilizer, with the tray portion in place therein, taken along line 4—4 of FIG. 1.
FIG. 5 is an enlarged scale cross-sectional view, partially in elevation, through the sterilizer, with the tray portion removed therefrom, taken along line 5—5 of FIG. 1.

The sterilizer 100 is also provided with a generally rectangularly configured stainless steel inner housing 124 having a front wall 126, top and bottom walls 128 and 130, left and right side walls 132 and 134, and a forwardly inset rear wall 136. As best illustrated in FIGS. 3 and 4, a jet curtain plate 140 is horizontally secured within the inner housing 124 and divides its interior into an air supply plenum 142 disposed beneath the plate, and a sterilization chamber 144 positioned above the plate. A central portion of the plate 140 is corrugated as illustrated, with a series of elongated air slots 146 being formed through the apexes of the upwardly projecting ridge portions 148 of the corrugations. A pair of generally inverted U-shaped tray support rods 150 are secured to the corrugated portion of plate 140 and project upwardly therefrom as illustrated.

Secured to the interior surface of the upper wall 128 of the inner housing 124 is a horizontally oriented deflection plate 152 having a corrugated, non-perforated central portion 154 positioned above the corrugated portion of the perforated jet curtain plate 140. A rectangular supply air opening 156 is formed through a lower left corner portion of the inner housing rear wall 136 (as viewed in FIG. 4) and is positioned below the jet curtain plate 140. A circular return air opening 158 is also formed through the rear wall 136 above the plate 140 and to the right of the supply air opening 156 (see also FIG. 2). The front wall 126 of the inner housing 124 is provided with a horizontally elongated rectangular opening 160 (FIG. 3) which communicates with the sterilization chamber 144 and is bordered by a forwardly projecting support flange 162.

Referring again to FIG. 2, to circulate heated sterilization air through the inner housing 124 in a manner subsequently described, a circulating fan, duct and heating coil assembly 164 is provided which includes a centrifugal supply fan 166 having a rearwardly projecting motor 168, a generally L-shaped supply duct 170 connected to the outlet of the fan and having a forwardly projecting open discharge end portion 172, and an electric heating element 174 operatively mounted within the duct 170. Assembly 164 is removably secured to the rear wall 136 of the inner housing 124 by means of threaded mounting studs 176 secured to the wall. Studs 176 extend rearwardly through mounting tabs 178 on the assembly 164 and into fastening nuts 180. With the assembly 164 removably secured to the rear wall 136 of the inner housing 124, a circular inlet opening (not illustrated) of the fan 166 is in registry with the back wall opening 158, and the open discharge end portion 172 of the supply duct 170 is received in the rectangular opening 156 in the wall 136.

The inner housing 124 and the fan and coil assembly 164 removably secured thereto are received within a uniquely configured insulating jacket structure 182 which has a hollow, generally rectangular configuration and, as illustrated in FIGS. 2 and 6, includes a front wall 184 having a horizontally elongated rectangular opening 186 formed therethrough, top and bottom walls 188 and 190, left and right side walls 192 and 194, and a removable back access wall 196. As best illustrated in FIG. 6, each of the six walls of the insulating jacket 182 is defined by a hollow, flexible outer shell having outer and inner portions 198 and 200, and a suitable flexible insulating material 202 captively retained in the internal pocket defined between the shell portions 198 and 200. While a variety of alternate materials could be used, the illustrated flexible shell is of a silicone impregnated fiberglass cloth material, while the internal insulation is of a flexible, fibrous insulating material.

To assemble the sterilizer 100, the inner housing 124, with the fan, duct and coil assembly 164 secured thereto as previously described, is inserted forwardly into the open rear end of the insulating jacket 182 until the front wall 126 of the inner housing abuts the interior surface of the front jacket wall 184 and the support flange 162 projects outwardly through the front jacket wall opening 186. The partially jacketed inner housing is then inserted forwardly through the open rear end of the outer housing 102 until the support flange 162 is received within an internal peripheral flange 204 (FIG. 3) that borders a horizontally elongated rectangular opening 206 formed inwardly through the front wall 104 (see FIG. 1 also) of the outer housing 102, and the bottom insulating jacket wall 190 rests upon the inner surface of the lower wall 108 of the outer housing 102. A suitable resilient gasket 207 is installed around the juncture between the flanges 162, 204 as indicated in FIGS. 3 and 5. The flanges 162 and 204 are then secured together by spot welds (not illustrated) or other suitable fastening means. Appropriate wiring interconnections between the control panel 122 and the electric heating element 174 are then made. The rear insulating jacket wall 196 is then brought into place over the exposed assembly 164, the fan motor 168 being received in and projecting outwardly through a generally Y-shaped slit 210 formed through the back jacket wall 196.

The jacket wall 196 is removably secured to the balance of the insulating jacket 182 by means of flexible tab portions 212 secured to the rear edges of the jacket walls 188, 190, 192 and 194 which are folded over onto the exterior surface of the jacket wall 196. The flaps 212 are removably fastened to the back jacket wall 196 by means of cooperating high temperature material hook and pile fastening surfaces 214 and 216 respectively formed on the flaps 212 and the rear jacket wall 196. Wiring to the coil 174 is conveniently passed outwardly through small slits 217, 218 formed along the lower edge of wall 196 and the lower tab 212. While the rear jacket wall 196 is illustrated as being completely removable from the balance of the jacket structure, it could of course be secured thereto along one edge if desired for pivotal outward movement to provide access to the interior of the jacket structure.

After the insulating jacket structure has been closed in this manner around the inner housing and the fan and coil assembly, and the wiring interconnections between the control panel 122 and the fan motor 168 and heating coil 174 have been completed, the rear outer housing wall 114 is secured to the back of the remaining outer housing portion with the screws 116 to ready the sterilizer 100 for operation.

Referring now to FIGS. 1, 2 and 4, dental instruments 220, or similar objects to be sterilized, are supported within the sterilization chamber 144 by means of a removable instrument support tray 222 having a rectangular frame portion 224 to which is secured a rectangular section of wire mesh 226 upon which the instruments 220 may be rested as depicted in FIGS. 1 and 4. A horizontally elongated rectangular metal plate 228 is secured to the front end of the frame 224 and has a resilient sealing gasket 230 secured around its periphery. A series of small magnets (not illustrated) are imbedded in the gasket 230. A second metal plate 232, configured similarly to plate 228, is spaced forwardly of plate 228 and secured thereto by a pair of cylindrical metal spacing elements 234. An elongated handle member 236 is secured at one end to the plate 32 and projects forwardly therefrom. With the instruments 220 positioned in a spaced relationship on the wire mesh 226, the frame portion 224 of tray 222 is rearwardly inserted into the sterilization chamber 144, through the housing opening 206 and the support flange 162 secured therein, so that the frame and wire mesh portions of the tray rests upon the tray supports 150 as depicted in FIG. 4. With the tray fully inserted in this manner, the gasket 230 is brought into engagement with the outer surface of the front housing wall 104 so that the gasket 230 forms an external seal around the housing opening 206. The magnets within the gasket 230 hold it in firm engagement with the outer surface of the front housing wall 104.

During operation of the sterilizer 100, the circulating fan 166 forces air through the supply duct 170 into the air supply plenum 142 (FIGS. 3 and 4) via the inner housing wall opening 156 beneath the plate 140, the air supplied to the plenum 142 being heated to a predetermined temperature by the electric heating element 174 within the supply duct 170. Heated air entering the plenum 142 is forced upwardly through the jet plate openings 146 and is discharged therefrom in the form of upwardly directed, relatively high velocity heated air impingement jets 238. As more fully described in my co-pending U.S. application Ser. No. 044,909, some of the jets impinge upon the lower surfaces of the instruments 220, while the remainder of the jets strike the corrugated portion 154 of the upper deflection plate 152 and are downwardly deflected therefrom in the form of relatively high velocity heated air jets which impinge upon upper surface portions of the instruments. This impingement upon opposite surfaces of the instruments 220 by the upwardly flowing and downwardly deflected heated air jets creates a turbulent layer of heated air around the instruments which causes the rapid sterilization and depyrogenation thereof. The sterilizing air is then rearwardly returned to the circulating fan 66 through the inner housing wall opening 158 to complete the air recirculation cycle.

It is theorized that the return flow of air from the turbulent air layer enveloping the instruments 220, in a direction generally perpendicular to the upwardly flowing and rearwardly deflected jets, significantly contributes to the overall rapid and complete sterilization and depyrogenation of the instruments. Specifically, it is believed that this transverse return air flow draws the turbulent impingement air horizontally across the instruments to produce a "scrubbing" action thereon which serves to more rapidly and thoroughly drive sterilizing air heat into the instruments.

As illustrated in FIGS. 3–5, the insulating jacket structure 182 defines with the interior surface of the outer housing 102 a cavity 240 which extends around the front, back, top and sides of the insulating jacket. To cool the interior of the sterilizer 100 around the inner housing 124, a flow of ambient cooling air 242 (FIGS. 3 and 5) is forced into the cavity 240 by means of a small cylindrical cooling fan 244 suitably secured to the interior surface of the removable back wall 114 of the outer housing 102. The cooling air 242 is drawn into the inlet of fan 244 through small inlet openings 246 formed in the wall 114 behind the fan. The cooling air is then radially discharged from the fan 244, flowed through the cooling cavity 240 around the insulating jacket 182 and is then discharged from the outer housing 102 through a series of elongated discharge slots 248 (FIGS. 2 and 5) formed through the outer housing bottom wall 108 adjacent its side and back walls 110, 112 and 114.

It can be seen from the foregoing that the sterilizer 100 provides markedly improved repair and maintenance access to the circulating fan 166, its motor 168, and the electric heating element 174 without the necessity of removing the inner housing 102 or providing maintenance access to any portion of its interior. Specifically, the entire circulating fan and heating coil assembly may be rapidly and easily removed from the sterilizer, without having to remove the inner housing therefrom, simply by removing the rear housing wall 114 and the rear insulating jacket wall 196, and then unbolting and removing the fan and coil assembly 164 for repair or replacement. Additionally, because of the unique construction and configuration of the insulating jacket structure 182, such easy and rapid access to the fan and coil assembly 164 is achieved without shredding or otherwise dislodging the actual insulating material 202 due to its captive retention within the flexible outer insulation shell. This, of course, positively prevents any extraneous bits of insulating material 202 from being entrained in the heated air stream and finding its way into the sterilization chamber 144.

The foregoing detailed description is to be clearly understood as being given by way of illustration and example only, the spirit and scope of the present invention being limited solely by the appended claims.

What is claimed is:

1. A recirculating hot air sterilizer comprising:
wall means for defining a sterilization chamber separated from a supply air plenum by a plate member having a series of jet-forming openings formed therethrough, said sterilization chamber being partially bounded by a deflection wall spaced apart from and extending generally parallel to said plate member;

support means for supporting objects to be sterilized within said sterilization chamber in a mutually spaced relationship with each other and in a spaced relationship with said plate member and said deflection wall, said jet-forming openings being positioned and arranged so as to both impinge high velocity air flowed therethrough, upon first surface portions of said objects supported on said support means and to bypass high velocity air around the supported objects; and hot air recirculating means for creating a recirculating hot air flow within said wall means which sequentially:

enters said supply air plenum;

is forced through said jet-forming openings to form a series of relatively high velocity impingement air jets directed toward said deflection wall so that a first number of said jets impinge upon first surface portions of objects supported by said support means within said sterilization chamber, and a second number of said jets bypass the supported objects, strike said deflection wall and are deflected thereby onto opposite surface portions of the objects in the form of redirected, relatively high velocity jets which form with said first number of said jets a turbulent, heated air layer around the objects, is drawn outwardly through said sterilization chamber in a direction generally transverse to said jets and said redirected jets to move said air layer across the objects in a direction generally transverse to said jets and said redirected jets, and is then returned to said supply air plenum, said wall means comprising an inner housing having a wall section extending along said sterilization chamber and said air supply plenum, said wall section having a return opening extending therethrough into said sterilization chamber, and a supply opening extending therethrough into said supply air plenum, said sterilizer further comprising an outer housing enveloping said inner housing and having an access wall section being movable to permit insertion of said inner housing into said outer housing and to permit access to said wall section of said inner housing, said inner and outer housings having aligned openings therein through which a portion of said support means may be inserted into said sterilization chamber, said hot air recirculating means including a fan, duct and heating element assembly removably secured to said wall section of said inner housing and including:

a recirculating fan having an outlet, and an inlet communicating with said sterilization chamber through said return opening, a supply duct connected to said outlet and having an open discharge end communicating with said supply air plenum through said supply opening, and a heating element operatively disposed within said supply duct; and an insulating jacket structure extending around and removably receiving said inner housing and said fan, duct and heating element assembly, said insulating jacket structure having a hollow shell portion captively retaining insulation therein, and having an access wall section being movable to permit insertion of said inner housing into the interior of said jacket structure.

2. The sterilizer of claim 1 wherein:
said hollow shell portion and said insulation are of flexible materials.

3. The sterilizer of claim 2 wherein:
said hollow shell flexible material is silicone impregnated fiberglass cloth material and said insulation flexible is material a flexible, fibrous material.

4. The sterilizer of claim 1 wherein:
said outer housing has an internal cooling cavity therein which envelopes a substantial portion of said insulating jacket structure, and
said sterilizer further comprises cooling means for flowing cooling air through said cavity.

5. The sterilizer of claim 4 wherein:
said outer housing has at least one cooling air discharge opening formed in a wall portion thereof, and
said cooling means include a cooling fan positioned and arranged to sequentially flow ambient air into said outer housing, through said cooling cavity and outwardly through said at least one cooling air discharge opening.

6. The sterilizer of claim 5 wherein:
said cooling fan is disposed within said outer housing and is carried by said access wall section for movement therewith.

7. A recirculating hot air sterilizing device comprising:
a hollow outer housing having a first wall portion with an opening formed therein through which objects to be sterilized may be inwardly inserted, and a second wall portion positioned and arranged so as to be movable to provide access to the interior of said outer housing;
a hollow inner housing positioned within said outer housing and having a first wall portion inwardly adjacent said first wall portion of said outer housing and having an entrance passage formed thereon which is generally aligned with said entrance opening in said first wall portion of said outer housing and adapted to receive objects to be sterilized, and a second wall portion spaced inwardly from said first wall portion of said inner housing;
support means for supporting objects to be sterilized within said inner housing;
hot air recirculating means for creating a recirculating hot air flow within said inner housing to sterilize objects supported therein by said support means, said hot air recirculating means including a recirculating fan secured to said second wall portion of said inner housing and having a motor positioned within said outer housing;
an insulating jacket structure positioned within said outer housing, said insulating jacket structure enveloping and removably receiving said inner housing, being insertable with said inner housing into said outer housing and having:
a hollow outer skin portion filled with and captively retaining an insulating material,
a first opening through which said entrance passage of said inner housing extends,
an access section extending exteriorly across said second wall portion of said inner housing and being removably secured to said jacket structure in a manner permitting said access section to be moved to form a second opening in said jacket structure through which said inner housing may be inserted and removed, said access section having an opening formed therethrough through which said motor outwardly extends, and
an exterior surface which defines within the interior surface of said outer housing a cooling cavity that envelopes a substantial portion of said jacket structure; and
cooling means for flowing a supply of cooling air through said cooling passage.

8. The sterilizing device of claim 7 wherein:
said hollow outer skin portion and said insulating material are each of a generally flexible material.

9. The sterilizing device of claim 8 wherein:
said outer skin flexible material is a silicone impregnated fiberglass cloth material, and said insulating flexible material is a fibrous insulating material.

10. The sterilizing device of claim 7 wherein:
said hot air recirculating means comprise a fan, duct and heating coil assembly removably and exteriorly secured to said second wall portion of said inner housing, said assembly including said recirculating fan, a supply duct secured to the outlet of said recirculating fan and communicating with the interior of said inner housing, and a heating coil operatively positioned within said heating duct, said recirculating fan having an inlet communicating with the interior of said inner housing.

11. The sterilizing device of claim 7 wherein:
said outer housing has at least one cooling air discharge opening formed in a wall portion thereof, and
said cooling means include a cooling fan adapted to sequentially flow ambient air into said outer housing, through said cooling cavity and outwardly through said at least one cooling air discharge opening.

12. The sterilizing device of claim 11 wherein:
said cooling fan is disposed within said outer housing and is carried by said second wall portion of said outer housing for movement therewith.

* * * * *